(12) United States Patent
van den Berg et al.

(10) Patent No.: US 6,593,479 B2
(45) Date of Patent: Jul. 15, 2003

(54) COATING COMPOSITION COMPRISING A BICYCLO- OR SPIRO-ORTHOESTER FUNCTIONAL COMPOUND

(75) Inventors: Keimpe Jan van den Berg, Duiven (NL); Klaus Hobel, Erlenbach (DE); Huig Klinkenberg, Katwijk aan Zee (NL); Arie Noomen, Voorhout (NL); Josephus Christiaan van Oorschot, Arnhem (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/935,308

(22) Filed: Aug. 22, 2001

(65) Prior Publication Data

US 2002/0161135 A1 Oct. 31, 2002

Related U.S. Application Data

(62) Division of application No. 08/804,485, filed on Feb. 21, 1997, now Pat. No. 6,297,329
(60) Provisional application No. 60/015,878, filed on Apr. 22, 1996.

(30) Foreign Application Priority Data

Feb. 23, 1996 (NL) ............................................. 1002427

(51) Int. Cl.$^7$ ............................................. C07D 319/14
(52) U.S. Cl. ........................................ 549/363; 549/378
(58) Field of Search ................................. 549/363, 378

(56) References Cited

U.S. PATENT DOCUMENTS

| | | | |
|---|---|---|---|
| 3,328,427 A | * 6/1967 | Melaas | |
| 4,338,240 A | 7/1982 | Mizutani et al. | ............. 524/284 |
| 4,378,524 A | 3/1983 | Steinmüller | ................. 324/107 |
| 4,788,288 A | * 11/1988 | Pinschmidt | |
| 4,798,745 A | 1/1989 | Martz et al. | ............. 427/407.1 |
| 4,864,055 A | * 9/1989 | Pinschmidt | |
| 5,155,170 A | 10/1992 | Baukema et al. | ......... 515/15 A |
| 5,214,086 A | 5/1993 | Mormile et al. | ............ 524/237 |
| 5,336,807 A | * 8/1994 | Burgoyne | |

FOREIGN PATENT DOCUMENTS

| | | | |
|---|---|---|---|
| DE | 1 595 673 | 9/1969 | |
| EP | 0 134 691 | 3/1985 | ............ C08G/59/42 |
| EP | 0 575 667 | 12/1993 | ............. C08F/8/08 |
| JP | 83-189211 | 11/1983 | ............ B32B/27/04 |
| JP | 84-164334 | 9/1984 | ......... C08F/212/60 |
| JP | 86-195120 | 8/1986 | ............ C08G/65/16 |
| JP | 87-192415 | 8/1987 | ......... C08E/212/14 |
| WO | 93/17060 | 9/1993 | ............ C08G/63/02 |

OTHER PUBLICATIONS

Corey, E. J., et al, A New General Synthetic Route to Bridged Carboxylic Ortho Esters, vol. 24, Tetrahedron Letters, 5571–5574 (1983).*
Corey, et al. "A New General Synthetic Rout to Bridged Carboxylic Orhto Esters", vol. 24, *Tetrahedron Letters*, 5571–5574 (1983).
Crivello, et al. "Structure and Reactivity Relationships in the Photoinitiated Cationic Polymerization of Oxetanne Monomers", *J.M.S.–Pure Appl. Chem.* 189–206 (1993).
Endo, et al. "Preparation and Ring–Opening Polymerization of Bicyclic Ortho Esters Containing Urethane Structures", *Polymer Journal* vol. 13, 715–718 (1991).
Gassman, et al. "The Ionic Diels–Alder Reaction of 1–Vinyl–4–methyl–2,6,7–trioabicyclo[2.2.2. ]octane Retention of the Ortho Ester Moiety through the Use of Trioxabicyclo[2.2.2.] octanyl Protecting Group", *J. Chem Soc., (Chem Commun.)*, 837–841 (1989).
LiBiassi, et al. "Photoinitiators for the Simultaneous Generation of Free Radicals and Acid Hardening Catalysts", *Specialty Catalysts* pp. 396, 399, 400, 402 (1997) (Reprinted from Radcure Conference '86).
Pattison "Cyclic Ethers Made By Pyrolysis of Carbonate Esters" *J. Am. Chem Soc'y*, 3455–3456 (1957).
Netherlands Search Report for: NL1002427; dated Oct. 16, 1996.
Derwent Abstract No: 67 11443 abstracting DE 1595673.
Derwent Abstract No: 83–841276/50 abstracting JP 83–189211.
Derwent Abstract No: 84–267189/43 abstracting JP 83–038316.
Derwent Abstract No: 86–268527/41 abstracting JP 86–195120.
Derwent Abstract No: 87–274739/39 abstracting JP 87–192415.

* cited by examiner

*Primary Examiner*—Robert D. Harlan
(74) *Attorney, Agent, or Firm*—Joan M. McGillycuddy

(57) ABSTRACT

The invention pertains to a coating composition comprising a first compound comprising at least one bicyclo- or spiro-orthoester group and a second compound comprising at least two hydroxyl-reactive groups. The invention also comprises a process for curing the present coating composition. More particularly, the latent hydroxyl groups of the bicyclo- or spiro-orthoester groups have to be deblocked and reacted with the hydroxyl-reactive groups of the second compound if the present coating composition is to be cured. Further, a process for making bicyclo-orthoester compounds from the corresponding oxetane compound is described, as are polymers comprising at least one bicyclo- or spiro-orthoester group.

3 Claims, No Drawings

COATING COMPOSITION COMPRISING A BICYCLO- OR SPIRO-ORTHOESTER FUNCTIONAL COMPOUND

This is a divisional of U.S. patent application Ser. No. 08/804,485, with a filing date of Feb. 21, 1997 now U.S. Pat. No. 6,297,329. This application also claims priority of Netherlands Patent Application No. NL 1002427, filed on Feb. 23, 1996 and U.S. Provisional Patent Application No. 60/015,878 filed on Apr. 22, 1996.

The invention pertains to a coating composition comprising a first compound comprising at least one bicyclo- or spiro-orthoester group.

BACKGROUND OF THE INVENTION

The use of compounds comprising bicyclo-orthoester groups in coating compositions is known from U.S. Patent publication No. 4,338,240. In this patent publication the use and the preparation of bicyclo-orthoester-functional compounds (hereinafter bicyclo-orthoester will be abbreviated to BOE) is described. Described are, e.g., BOE-functional compounds, which are the adduct of two compounds comprising one hydroxyl group and one BOE group and one compound comprising two isocyanate groups. The compounds are cross-linked by means of cationic ring opening homopolymerization of the BOE groups. In that case, however, the presence of moisture has to be excluded. Furthermore, energy in the form of ultraviolet, infrared or microwave irradiation or heat has to be supplied during the polymerization process.

SUMMARY OF THE INVENTION

The invention now provides a coating composition of the aforementioned type which is free of said drawbacks. For that reason the coating composition mentioned in the opening paragraph is characterized in that it comprises a second compound comprising at least two hydroxyl-reactive groups.

A coating composition comprising a compound comprising at least one bicyclo- or spiro-orthoester group (hereinafter spiro-orthoester will be abbreviated to SOE) is a composition having latent hydroxyl groups. In the presence of water or moisture from the air the BOE or SOE groups will be hydrolyzed, forming hydroxyl groups. This reaction is also known as deblocking. During deblocking few if any volatile components are released. When the BOE- or SOE-group is deblocked in this manner, it is not possible to obtain a homopolymer of BOE- or SOE groups by cationic polymerization. However, it has now been found that when a second compound comprising at least two hydroxyl-reactive groups is present in the composition, the deblocked hydroxyl groups can react with the hydroxyl-reactive groups to give a cross-linked polymer.

BOE- and SOE-functional compounds may be used as main binders or as reactive diluents in the coating compositions of the present invention.

The use of compounds comprising BOE or SOE groups in coating compositions has several advantages over the use of compounds having free hydroxyl groups, such as hydroxyl-functional reactive diluents, hydroxyl-functional main binders, e.g. polyester polyols and acrylate polyols, and even compounds where the BOE or SOE groups have already been hydrolyzed.

Firstly, the viscosity of compounds comprising BOE or SOE groups is lower than that of the corresponding hydrolyzed compounds. In consequence, less viscosity-reducing solvent which evaporates in air is needed in the coating composition.

Secondly, because of the stability of the BOE- and SOE-functional compounds the pot life:drying time ratio of compositions according to the invention is particularly favorable, for hydrolysis only takes place in the presence of water or moisture.

Thirdly, in coating compositions of the present invention BOE- and SOE functional compounds have the advantage that hydrolysis of the BOE or SOE group produces a substantial increase in the composition's viscosity. A high viscosity will give reduced sagging of the coating composition on the substrate.

Finally, it has been found that the coating compositions of the present invention provide a high build behavior.

DETAILED DESCRIPTION OF THE INVENTION

By BOE groups are meant in this connection groups having a structure according to formula I

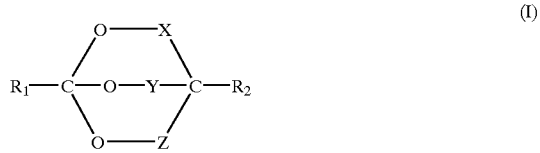

wherein
- X and Z are independently from each other selected from linear or branched alk(en)ylene groups with 1–4 carbon atoms optionally containing an oxygen or a nitrogen atom;
- Y is nothing or is selected independently of X and Z from linear or branched alk(en)ylene groups with 1–4 carbon atoms optionally containing an oxygen or a nitrogen atom;
- $R_1$ and $R_2$ may be the same or different and are selected from the group of monovalent radicals comprising
- hydrogen, hydroxyl, alk(en)yl groups comprising 1–30 carbon atoms which may be linear or branched and may optionally contain one or more heteroatoms and groups selected from the group of oxygen, nitrogen, sulphur, phosphorus, sulphone, sulphoxy, and ester, optionally substituted with epoxy, cyano, amino, thiol, hydroxyl, halogen, nitro, phosphorus, sulphoxy, amido, ether, ester, urea, urethane, thioester, thioamide, amide, carboxyl, carbonyl, aryl, and acyl groups, and
- divalent radicals comprising
- alk(en)ylene groups having 1–10 carbon atoms which groups may be linear or branched and may optionally contain one or more heteroatoms and groups selected from the group of oxygen, nitrogen, sulphur, phosphorus, sulphone, sulphoxy, and ester, optionally substituted with epoxy, cyano, amino, thiol, hydroxyl, halogen, nitro, phosphorus, sulphoxy, amido, ether, ester, urea, urethane, thioester, thioamide, amide, carboxyl, carbonyl, aryl, and acyl groups, ester groups; ether groups; amide groups; thioester groups; thioamide groups; urethane groups; urea groups; and a single bond.

Preferably, X, Y, and Z are methylene. $R_1$ and $R_2$ in that case are linked to a divalent 2,6,7-trioxabicyclo[2.2.2]octane radical.

In the case of $R_1$ and $R_2$ being both monovalent radicals, the BOE group as defined by formula I is the same as the BOE-functional compound. Monovalent radicals $R_1$ and $R_2$ are preferably independently from each other selected from the group of hydrogen, hydroxyl, and linear or branched alk(en)yl groups having 1–20 carbon atoms, optionally substituted with one or more hydroxyl groups and optionally comprising an ester group. Examples of such groups are: methyl, methylol, ethyl, ethylol, propyl, propylol, butyl, pentyl, hexyl, heptyl, octyl, nonyl, decyl, undecyl, a —CH$_2$—CH$_2$—O—CO—C$_{1\text{-}20}$ alk(en)yl group, and mixtures thereof.

Preferably, R$_1$ is linear or branched alk(en)yl having 1–20 carbon atoms, optionally substituted with hydroxyl, while R$_2$ is methyl or ethyl. Alternatively, R$_1$ can be methyl, ethyl, propyl, butyl, pentyl, hexyl, heptyl, octyl, nonyl, decyl, undecyl, and mixtures thereof, while R$_2$ can be methylol, ethyl, ethylol or a —CH$_2$—CH$_2$—C—CO—C$_{1\text{-}20}$ alk(en)yl group.

When a divalent radical is selected for either or both R$_1$ or R$_2$ groups, high-molecular weight BOE-functional compounds can be formed. These may be adducts or polymers comprising several BOE groups. Thus two BOE groups can form an adduct by selecting a monovalent radical for one of the two R$_1$ and R$_2$ groups, and a divalent radical for the other. The BOE groups will then be linked together via the divalent radical. BOE groups may also be linked via the divalent radicals to monomer or oligomer compounds. Such BOE-functional compounds are, e.g. described in above-mentioned U.S. Pat. No. 4,338,240. For example, two BOE groups may be linked to a dimer fatty acid, e.g. "PRIPOL®" 1009 (available from Unichema Chemie BV, Gouda, Netherlands). Alternatively, in the aforementioned configuration the BOE groups can function as side groups or terminal groups in a polymer chain. The polymers can be, e.g., polyesters, polyethers, polyacrylates, polyamides or polyurethanes. When the divalent radical is a single bond, the BOE group is bonded directly to the polymer. When the R$_1$ and R$_2$ groups are both divalent, the BOE groups can be incorporated into the main chain of a polymer or they can serve to link two polymer chains together. Preferably, one or both R$_1$ and R$_2$ groups are selected from the group of ester, ether, urethane, a single bond, and alk(en)ylene groups having 1–10 carbon atoms which may be linear or branched and may contain one or more ester, ether, or urethane groups.

The term SOE groups in this case refers to groups having a structure according to formula II or III

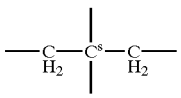

(II)

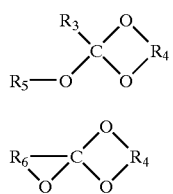

(III)

wherein
R$_3$ and R$_5$ are independently from each other selected from the group of linear or branched alk(en)yl, aryl or acyl optionally containing one or more oxygen, nitrogen, sulphur or phosphorus atoms, optionally substituted with a halogen atom; and R$_4$ and R$_6$ are independently from each other selected from an alkylene group having 1–3 carbon atoms optionally substituted with one or more groups selected from monovalent radicals such as linear or branched alk(en)yl, aryl or acyl groups optionally containing one or more oxygen, nitrogen, sulphur, and phosphorus atoms; and divalent radicals such as a single bond and an alkylene group having 1–10 carbon atoms with or without one or more atoms and groups selected from oxygen, nitrogen, sulphur, and phosphorus atoms, and ether, ester, and urethane groups.

Preferably, R$_3$ and R$_5$ are selected independently from linear or branched alk(en)yl groups having 1–4 carbon atoms, e.g., a methyl or ethyl group.

In the case that neither of R$_4$ and R$_6$ is substituted with a divalent radical, the SOE group as defined by formulae II and III is the same as the SOE-functional compound.

When a divalent radical is selected as substituent for either or both R$_4$ and R$_6$ groups, high-molecular weight SOE-functional compounds can be prepared in the same manner as described above for high-molecular BOE compounds. When R$_4$ or R$_6$ has one divalent radical substituent, adducts or polymers can be made which have SOE groups as terminal or side groups. In formula III, R$_4$ and R$_5$ can both have divalent radicals as substituents, in which case the SOE group can be incorporated into the main chain. The polymers may be, e.g., polyacrylate, polyester, polyether, polyamide or polyurethane.

Alternatively, R$_4$ can be

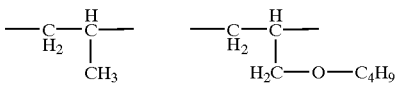

with the compound formed being point symmetrical to C$^S$, giving a SOE compound according to formula IV:

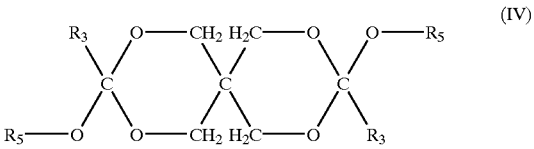

(IV)

Preferably, formula IV is:

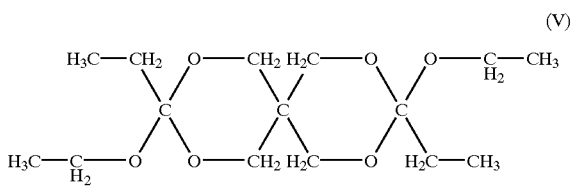

(V)

Preferably, R$_4$ is ethylene, optionally substituted with a linear or branched alkyl group having 1–5 carbon atoms, optionally containing one or more oxygen and nitrogen atoms. For instance, R$_4$ may be:

—C—C—    —C—C—
H$_2$ |     H$_2$ |
    CH$_3$     H$_2$C—O—C$_4$H$_9$

Preferably, R$_6$ is propylene.

In addition to the BOE- or SOE-functional compound the coating composition according to the invention comprises a second compound comprising at least two hydroxyl-reactive groups. The hydroxyl-reactive groups are selected from the group of isocyanate, epoxy, acetal, carboxyl, anhydride, and alkoxy silane groups. Also, mixtures of these groups in one compound are included. Alternatively, the second compound can be an amino resin.

Examples of compounds comprising at least two isocyanate groups are aliphatic, alicyclic, and aromatic polyisocyanates such as trimethylene diisocyanate, 1,2-propylene diisocyanate, tetramethylene diisocyanate, 2,3-butylene diisocyanate, hexamethylene diisocyanate, octamethylene diisocyanate, 2,4-trimethyl hexamethylene diisocyanate, 2,4,4-trimethyl hexamethylene diisocyanate, dodecamethylene diisocyanate, α,α'-dipropyl ether diisocyanate, 1,3-cyclopentylene diisocyanate, 1,2-cyclohexylene diisocyanate, 1,4-cyclohexylene diisocyanate, 4-methyl-1,3-cyclohexylene diisocyanate, 4,4'-dicyclohexylene diisocyanate methane, 3,3'-dimethyl-4,4'-dicyclohexylene diisocyanate methane, m- and p-phenylene diisocyanate, 1,3- and 1,4-bis(isocyanate methyl) benzene, 1,5-dimethyl-2,4-bis(isocyanate methyl) benzene, 1,3,5-triisocyanate benzene, 2,4- and 2,6-toluene diisocyanate, 2,4,6-toluene triisocyanate, α,α,α',α'-tetramethyl o-, m-, and p-xylylene diisocyanate, 4,4'-diphenylene diisocyanate methane, 4,4'-diphenylene diisocyanate, 3,3'-dichloro-4,4'-diphenylene diisocyanate, naphthalene-1,5-diisocyanate, isophorone diisocyanate, and transvinylidene diisocyanate and mixtures of the aforementioned polyisocyanates.

Also, such compounds may be adducts of polyisocyanates, e.g., biurets, isocyanurates, allophonates, uretdiones, and mixtures thereof. Examples of such adducts are the adduct of two molecules of hexamethylene diisocyanate or isophorone diisocyanate and a diol such as ethylene glycol, the adduct of 3 molecules of hexamethylene diisocyanate and 1 molecule of water, the adduct of 1 molecule of trimethylol propane and 3 molecules of isophorone diisocyanate, the adduct of 1 molecule of pentaerythritol and 4 molecules of toluene diisocyanate, the isocyanurate of hexamethylene diisocyanate, available from Bayer Aktiengesellschaft (Federal Republic of Germany) under the trade designation "DESMODUR®" N3390, the uretdione of hexamethylene diisocyanate, available from Bayer under the trade designation "DESMODUR®" N3400, the allophonate of hexamethylene diisocyanate, available from Bayer under the trade designation "DESMODUR®" LS2101, and the isocyanurate of isophorone diisocyanate, available from Hüls under the trade designation "VESTANATE™" T1890. Furthermore, (co)polymers of isocyanate-functional monomers such as α,α'-dimethyl-m-isopropenyl benzyl isocyanate are suitable for use. Finally, the above-mentioned isocyanates and adducts thereof may be present in the form of blocked isocyanates as known to the skilled man.

Examples of compounds comprising at least two epoxy groups are solid or liquid epoxy compounds, such as the di- or polyglycidyl ethers of aliphatic, cycloaliphatic, or aromatic hydroxyl compounds such as ethylene glycol, glycerol, cyclohexane diol, mononuclear di- or polyvalent phenols, bisphenols such as Bisphenol-A and Bisphenol-F, and polynuclear di- or polyvalent phenols; polyglycidyl ethers of phenol formaldehyde novolac; epoxidized divinyl benzene; epoxy compounds comprising an isocyanurate group; an epoxidized polyalkadiene such as epoxidized polybutadiene; hydantoin epoxy resins; epoxy resins obtained by epoxidizing aliphatic and/or cycloaliphatic alkenes, such as dipentene dioxide, dicyclopentadiene dioxide, and vinylcyclohexene dioxide; and glycidyl groups-comprising resins, such as polyesters or polyurethanes having two or more glycidyl groups per molecule; or mixtures of the aforementioned epoxy compounds. Preferably, use is made of the aforementioned cycloaliphatic compounds comprising two or more epoxy groups.

Alternatively, use is made of a (co)polymer of ethylenically unsaturated epoxy groups comprising compounds such as glycidyl(meth)acrylate, N-glycidyl(meth)acrylamide and/or allyl glycidyl ether and, if so desired, one or more copolymerizable, ethylenically unsaturated monomers.

Examples of compounds comprising at least two acetal groups are disclosed, int. al., in patent publications U.S. Pat. No. 4,788,288, U.S. Pat. No. 4,864,055, U.S. Pat. No. 5,155,170, and U.S. Pat. No. 5,336,807. Other suitable acetal-functional compounds include compounds obtained by reacting aminobutyraldehyde di(m)ethyl acetal (ABDA) and carboxyl ester-, isocyanate- or cyclocarbonate-functional (co)oligomers or (co)polymers, e.g., polyester, polyacrylate, and polyurethane. An example of such a polymer includes the copolymer of glycerol cyclocarbonate methacrylate and styrene. Also, mixtures of compounds comprising at least two acetal groups can be employed.

Examples of compounds comprising at least two carboxyl groups include saturated or unsaturated aliphatic, cycloaliphatic, and aromatic polycarboxylic acids, such as malonic acid, succinic acid, adipic acid, azelaic acid, sebacic acid, decane dicarboxylic acid, dimer fatty acid, maleic acid, tetrahydrophthalic acid, hexahydrophthalic acid, hexahydroendomethylene tetrahydrophthalic acid, phthalic acid, isophthalic acid, terephthalic acid, trimellitic acid, pyromellitic acid, 3,6-dichlorophthalic acid, tetrachlorophthalic acid, and mixtures thereof.

Examples of anhydride-functional compounds include radical polymers of an unsaturated cyclic anhydride monomer, e.g., maleic acid anhydride, itaconic acid anhydride, or citraconic acid anhydride. Furthermore, copolymers of said anhydride monomers and one or more ethylenically unsaturated monomers can be employed. These copolymers may contain 10–50 wt. % of anhydride groups. Examples of ethylenically unsaturated monomers are styrene, substituted styrene, vinyl chloride, vinylacetate, and esters of acrylic or methacrylic acid, e.g., methyl(meth)acrylate, ethyl(meth)acrylate, propyl(meth)acrylate, isopropyl(meth)acrylate, butyl(meth)acrylate, t-butyl(meth)acrylate, n-hexyl(meth)acrylate, 2-ethylhexyl(meth)acrylate, cyclohexyl(meth)acrylate, 2,2,5-trimethyl cyclohexyl(meth)acrylate, and isobornyl(meth)acrylate. The anhydride-functional (co)polymer may contain small quantities, e.g., 1 to 10 wt. %, of ethylenically unsaturated carboxylic acid groups, e.g., (meth)acrylic acid. The molecular weight of the anhydride-functional (co)polymer preferably is 1,000–50,000.

When the coating composition according to the present invention is used as a top coat, the aforesaid ethylenically unsaturated monomer preferably is used in a molar ratio of 1:1 with the anhydride monomer, as described in U.S. Pat. No. 4,798,745.

Alternatively, the anhydride-functional compound can be an adduct of an anhydride monomer and a functional group-comprising polymer. Examples of such adducts are: the adduct of polybutadiene or a butadiene/styrene copolymer and maleic acid anhydride; the adduct of maleic acid anhydride and a styrene/allyl alcohol copolymer esterified with an unsaturated fatty acid, resins of terpene and maleic acid anhydride; adducts of hydroxyl-comprising polymers and anhydride monomers, e.g., copolymers of hydroxyethyl (meth)acrylate or styrene/allyl alcohol and a tricarboxylic compound capable of forming anhydride groups, such as described in EP-A-0 025 917; the adduct of trimellitic acid anhydride and a polyol, such as described in EP-A-0 134 691; and the adduct of a thiol groups-comprising polymer and an unsaturated cyclic anhydride such as maleic acid anhydride, itaconic acid anhydride or citraconic acid anhydride. Also, mixtures of anhydride-functional compounds can be employed.

Examples of alkoxysilane-functional compounds are alkoxysilanes of the following general formula:

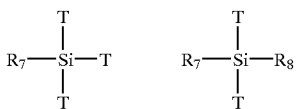

wherein T is a hydrolyzable group such as —OCH$_3$, —OC$_2$H$_5$ or —OC$_2$H$_4$OCH$_3$ and R$_7$ and R$_8$ are reactive groups selected independently from each other. Examples of such reactive groups include vinyl, aminoalkyl, epoxyalkyl, and methacryloxyalkyl groups. Also, reaction products of alkoxysilane-functional compounds and mixtures of alkoxysilane-functional compounds and/or reaction products of these can be employed.

Examples of vinyl-functional alkoxysilanes include vinyl triethoxysilane and vinyl trimethoxysilane As an example of a reaction product of a vinyl-functional alkoxysilane may be mentioned the silicone resin formed by the reaction of (CH$_2$=CHSiO$_{3/2}$)$_x$(R$_2$SiO)$_y$ and styrene.

Reaction products of amino-functional alkoxysilanes can be made by reacting such silanes with inorganic acids HA:

NH$_2$(CH$_2$)$_3$Si(T)$_3$+HA→A→NH(CH$_2$)$_3$Si(T)$_3$ wherein A is the acid radical ion, or with esters of organic acids R$_9$(COOR$_{10}$)$_n$, wherein n is an integer of at least 1, R$_9$ is a linear or branched, optionally unsaturated, alkane radical, and R$_{10}$ is a lower alkyl group, e.g., a C$_{1-4}$ alkyl group, e.g.:

NH$_2$(CH$_2$)$_3$Si(T)$_3$+R$_9$COOR$_{10}$→R$_9$CO—NH(CH$_2$)$_3$Si(T)$_3$

2NH$_2$(CH$_2$)$_3$Si(T)$_3$+1R$_{10}$OOCR$_9$COOR$_{10}$→

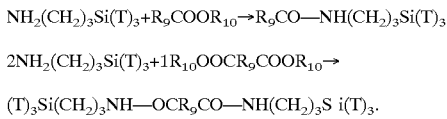

For example, the adduct of 1 mole diethyl malonate and 2 moles of 3-amino propyl trimethoxy silane is a suitable alkoxy silane containing compound. Also suitable for use are reaction products of amino-functional alkoxysilanes and isocyanate-functional compounds.

One example of a reaction product of an epoxy-functional silane compound is the reaction product of β-(3,4-epoxycyclohexyl) ethyl trimethoxysilane and amines, acids, and alcohols.

Examples of reaction products of methacryloxyalkyl trialkoxysilane are reaction products of γ-methacryloxypropyl trimethoxysilane and γ-methacryloxypropyl tri(β-methoxyethoxy)silane and vinyl-functional monomers, such as styrene and methyl methacrylate.

Examples of suitable amino resins are urea resins, guanamine resins, and melamine resins, and mixtures of these. Examples of urea resins are etherified methylol urea, butyl urea, and isobutyl urea. One example of a guanamine resin is tetra(methoxymethyl)benzoguanamine. Examples of melamine resins are hexa(methoxymethyl)melamine (HMMM) and isobutylated melamine.

In addition to the disclosed BOE- and SOE-functional compounds and said hydroxyl-reactive compounds other compounds may be present in the coating composition according to the present invention. Such compounds may be main binders and/or reactive diluents comprising reactive groups which may be cross-linked with the aforesaid hydroxyl-functional compounds and/or hydroxyl-reactive compounds. Examples include hydroxyl-functional binders, e.g., polyester polyols such as described in H. Wagner et al., *Lackkunstharze*, 5th ed., 1971 (Carl Hanser Verlag, Munich), polyether polyols, polyacrylate polyols, polyurethane polyols, cellulose acetobutyrate, hydroxyl-functional epoxy resins, alkyds, and dendrimeric polyols such as described in WO 93/17060. Also, hydroxyl-functional oligomers and monomers, such as castor oil and trimethylolpropane may be present. Finally, ketone resins, aspargyl acid esters, and latent or non-latent amino-functional compounds such as oxazolidines, ketimines, aldimines, diimines, secondary amines, and polyamines may be present. These and other compounds are known to the skilled person and are mentioned, int. al., in U.S. Pat. No. 5,214,086.

The ratio of hydroxyl-reactive groups to hydroxyl groups ranges from 50 to 300 eq. %, preferably from 70 to 250 eq. %

The invention further encompasses a process for curing the present coating composition. More particularly, the latent hydroxyl groups of the BOE or SOE-functional compound have to be deblocked and reacted with the hydroxyl-reactive groups of the second compound to allow the present coating composition to be cured.

The deblocking of the latent hydroxyl groups of the BOE and SOE compounds takes place under the influence of water in the form of, e.g., moisture from the air or added water. This deblocking is preferably catalyzed by a first catalyst selected from the group of Lewis acids, such as AlCl$_3$, SbCl$_5$, BF$_3$, BCl$_3$, BeCl$_2$, FeCl$_3$, FeBr$_3$, SnCl$_4$, TiCl$_4$, ZnCl$_2$ and ZrCl$_4$ and organic complexes thereof, e.g., BF$_3$-Et$_2$O, BF$_3$-2CH$_3$COOH, BF$_3$-2H$_2$O, BF$_3$—H$_3$PO$_4$, BF$_3$—(CH$_3$)$_2$O, BF$_3$—THF, BF$_3$-2CH$_3$OH, BF$_3$-2C$_2$H$_5$OH, and BF$_3$—C$_6$H$_5$CH$_2$, and Brønsted acids. Preferably, use is made of Brønsted acids having a pKa<3, such as a mono- or dialkyl phosphate, a carboxylic acid having at least one chlorine and/or fluorine atom, an alkyl or aryl sulphonic acid or an (alkyl)phosphoric acid, more particularly methane sulphonic acid, paratoluene sulphonic acid, optionally substituted naphthalene sulphonic acids, dodecyl benzene sulphonic acid, dibutyl phosphate, trichloroacetic acid, phosphoric acid, and mixtures thereof.

Said first catalysts may be blocked, if so desired, resulting in the release of the Lewis or Brønsted acid under the influence of, e.g., electromagnetic irradiation (light or UV), heat or moisture. Acid generating photoinitiators are described, int. al., in G. Li Bassi et al., "Photoinitiators for the Simultaneous Generation of Free Radicals and Acid Hardening Catalysts," *Radcure '86 Proceedings,* e.g. 2-methyl-1-[4-(methylthio)phenyl]-2-[4-methylphenylsulphonyl]propan-1-one (MDTA), ex. Fratelli Lamberti Spa, Varese, Italy. Alternatively, use may be made of Lewis acid generating compounds such as "IRGA-CURE®" 261 (available from Ciba Geigy, Tarrytown, N.Y.) and trimethyl silyl benzene sulphonic ester.

The first catalyst can be used alone or as a mixture of catalysts in effective amounts. The term effective amount in this case is dependent on the use of the BOE- or SOE-functional compound. When the BOE- or SOE-functional compound is used as a main binder, sufficient catalyst will have to be present to hydrolyze practically all BOE- or SOE-functional compounds. However, if the BOE- or SOE-functional compound is used primarily as a reactive diluent while other compounds are present as main binders, the hydrolyzation of at least a portion of the BOE- or SOE-functional compound will suffice.

Amounts of 0 to 10 wt. % relative to the BOE- and SOE-functional compounds of the first catalyst may be sufficient. Preferably, 0.3 to 8 wt. %, more specifically, 0.5 to 6 wt. %, will be present.

The reaction of the deblocked hydroxyl groups of the BOE or SOE compound, the hydroxyl-reactive groups of the second compound, and, optionally, third compounds present in the composition comprising hydroxyl groups or hydroxyl-reactive groups, takes preferably place under the influence of a second catalyst. Such catalysts are known to the skilled person. The second catalyst is used in an amount of 0 to 10 wt. %, preferably 0.001 to 5 wt. %, more preferably in an amount of 0.01 to 1 wt. %, calculated on solid matter (i.e., the amount of BOE or SOE, the hydroxyl-reactive compound, and, optionally, the above-mentioned third compounds).

As an example for the various hydroxyl-reactive groups the following catalysts may be mentioned. Polyisocyanates: dimethyl tin dilaurate, dibutyl tin dilaurate, dibutyl tin diacetate, tin octoate, zinc octoate, aluminum chelate, and dimethyl tin dichloride; polyepoxy compounds: tertiary amines and Lewis acids such as $BF_3$ or organic complexes thereof; polyacetal compounds: paratoluene sulphonic acid and dodecyl benzene sulphonic acid; polycarboxylic compounds: dodecyl benzene sulphonic acid, polyanhydride compounds: organotin compounds; alkoxysilane compounds: organotin compounds, phosphoric acid, paratoluene sulphonic acid, dodecyl benzene sulphonic acid, and tertiary amines; and amino resins: dodecyl benzene sulphonic acid.

As can be noted from the above, the first and the second catalyst may be the same in some coating compositions. In that case, the amount of catalyst may be higher than indicated for the first or second catalyst alone.

The coating composition according to the invention may be part of a components system, for instance a 2-component system. For example, one component may comprise both the BOE- or SOE-functional compound and the hydroxyl-reactive compound. The second component may comprise the catalyst for the hydrolysis of the BOE- or SOE-functional compound.

Alternatively, a 3-component system may be employed. For example, one component may comprise the BOE- or SOE-functional compound. A second component may comprise the hydroxyl-reactive component. A third component may comprise the catalyst for the hydrolysis of the BOE- or SOE-functional compound.

In addition, a coating composition such as described may contain the usual additives such as solvents, pigments, fillers, leveling agents, emulsifiers, anti-foaming agents and rheology control agents, reducing agents, antioxidants, HALS-stabilisers, UV-stabilizers, water traps such as molecular sieves, and antisettling agents.

Application onto a substrate can be via any method known to the skilled person, e.g., via rolling, spraying, brushing, flow coating, dipping, and roller coating. Preferably, a coating composition such as described is applied by spraying.

The coating composition of the present invention may be applied to any substrate. The substrate may be, for example, metal, e.g., iron, steel, and aluminum, plastic, wood, glass, synthetic material, paper, leather, or another coating layer. The other coating layer may be comprised of the coating composition of the current invention or it may be a different coating composition. The coating compositions of the current invention show particular utility as clearcoats (over base coats, water-borne and solvent-borne), base coats, pigmented topcoats, primers, and fillers. The compositions are particularly suitable for refinishing motor vehicles and transportation vehicles and in finishing large transportation vehicles such as trains, trucks, buses, and airplanes.

The applied coating composition can be cured very effectively at a temperature of, e.g., 0–50° C. If so desired, the coating composition may be baked, e.g., at a temperature in the range of 50–120° C. The present BOE-functional compound can be prepared in several ways.

One such way is the transesterification of a polyol in an appropriate solvent. Examples of such polyols include glycerol, trimethylol propane, and pentaerythritol. The transesterification agent can be a trialkyl orthoester selected from the group of triethyl orthoformate, triethyl orthoacetate, and triethyl orthopropionate. Preferably, use is made of solvents which are inert to the transesterification reaction, e.g., diethylene glycol dimethyl ether and tetraethylene glycol dimethyl ether. The catalyst for such a reaction may be a strong acid, e.g., paratoluene sulphonic acid or $BF_3Et_2O_1$. Such a process is described in T. Endo et al., *Polymer Journal*, Vol. 13 (1981), p. 715.

When the polyol selected is pentaerythritol, a BOE group comprising a hydroxyl group is formed. This BOE group is converted into a BOE-functional compound by means of a transesterification reaction or by reaction with an acid chloride. In this way a hydroxyl-functional BOE group can be linked via transesterification to a saturated or unsaturated carboxylic acid, preferably one having not more than 20 carbon atoms. The resulting BOE-functional compound has the advantage of being non-volatile or hardly volatile because of the high molecular weight, while, surprisingly, the viscosity remains low. For this reason the BOE-functional compound is highly suited to be used as a reactive diluent. When the carboxylic acid group is unsaturated, the present coating composition comprising such a BOE-functional compound can be cured in two ways, i.e., via the hydrolyzed BOE group as described above and via the unsaturated compound.

Also, the aforesaid hydroxyl-functional BOE group can be provided with a vinyl group via a transesterification reaction with a (meth)acrylate. By polymerization under the influence of radicals using a vinyl-comprising BOE a BOE-functional polyacrylate can be prepared.

A BOE-functional polyacrylate can further be prepared by the transesterification of a polyacrylate with a hydroxyl-functional BOE group. In this case it is preferred to employ a polyacrylate having short-chain esters, preferably esters having 1–4 carbon atoms. The advantage of such a polyacrylate is that after the transesterification reaction the resulting alcohol groups can be isolated, e.g., by distillation In general, every polymer having an ester group as side group can be provided with BOE groups via said transesterification. As examples of polymers may be mentioned polyesters, polyethers, polyamides, and polyurethanes.

Alternatively, the hydroxyl-functional BOE group can be provided with groups which are reactive or not using, e.g., isocyanate-functional compounds. Furthermore, two or more BOE-functional groups can be interlinked using a di- or polyisocyanate-functional compound. In this way also the hydroxyl-functional BOE group can be linked to, e.g., hydroxyl-functional polymers, e.g., polyester polyols, polyether polyols, and polyacrylate polyols.

Also, BOE-functional compounds can be prepared by converting the corresponding ester-functional oxetane compounds with $BF_3Et_2O_1$ as described by E. J. Corey et al., *Tetrahedron Letters*, 24 (1983), pp. 5571–5574.

Oxetane compounds have the following structure:

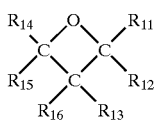

wherein $R_{11}$, $R_{12}$, $R_{13}$, $R_{14}$, and $R_{15}$ are independently from each other selected from the group of hydrogen and a linear or branched alkyl group having 1–10 carbon atoms; and $R_{16}$ is a linear or branched alkyl group having 1–4 carbon atoms substituted with a nucleophilic group selected from the group of hydroxyl, mercaptan, and a primary or secondary amine, and/or with an electrophilic group selected from halogen and derivatives of methane sulphonate, p-toluene sulphonate, and trifluormethane sulphonate.

Preferably, $R_{16}$ is hydroxymethyl, hydroxyethyl, chloromethyl or chloroethyl. The preparation of oxetane compounds comprising a hydroxyl group is described in J. B. Pattison, *J. Am. Chem. Soc.*, 79 (1957), pp. 3455–3456.

Said hydroxyl-functional oxetane compounds can be converted into ester group-comprising oxetanes via a transesterification reaction with suitable esters $R_{17}(COOR_{18})_n$, wherein n is an integer of at least 1, $R_{17}$ is a saturated or unsaturated alkyl, aryl, or acyl radical having 1–40 carbon atoms, optionally substituted with a reactive group such as vinyl, carbonyl, carboxyl ester, or hydroxyl, and $R_{18}$ is an alkyl group having 1–4 carbon atoms. $R_{18}$ preferably is methyl, ethyl, or propyl. The alcohols $R_{18}OH$ released on transesterification are isolated from the reaction mixture, e.g., by means of distillation. Such suitable esters may be, for example, the methyl ester of a fatty acid and mixtures of fatty acid, e.g. "EDENOR®" ME C6-10 (available from Henkel Kommanditgesellschaft auf, Dusseldorf, Federal Republic of Germany), and the dimethyl ester of a dimer fatty acid, e.g. "PRIPOL®" 1009, ex. Unichema.

Also, ester group-comprising oxetane compounds can be polymers, with the oxetane compounds being terminal groups or side groups. In that case, $R_{17}$ can be a polymeric group such as polyester, polyether, polyacrylate, polyamide or polyurethane. Suitable polyesters can be obtained by the nucleophilic addition of carbanions to α,β-unsaturated carbonyl compounds. Likewise suitable are ester group terminated polyesters derived from polycarboxylic acids, polyols, or ester-forming equivalents thereof. Preferably, the aforesaid $R_{18}$ groups are employed.

Other examples include the adduct of the conversion of diethyl fumarate and diethyl malonate to tetraethyl ester of 1,1,2,3-propane tetracarboxylic acid and a hydroxyl-functional oxetane. In the presence of a diol or polyol a terminal oxetane-functional polyester is formed.

The hydroxyl-functional oxetane compounds also can be converted with the aid of acid chlorides $R_{17}(COCl)_n$.

Preferably, $R_{17}$ is a group having a high molecular weight, such as pentyl, hexyl, heptyl, octyl, nonyl, decyl, undecyl, or the aforesaid polymers. The resulting BOE compound is non-volatile or hardly volatile because of the high molecular weight, and on account of its surprisingly low viscosity is pre-eminently suited to be used as a reactive diluent.

Halogen-functional oxetanes can be converted into ester-functional oxetanes by reacting them with carboxylate salts of, e.g., silver or with ammonium compounds such as substituted or unsubstituted ammonium salts.

It has now been found that the conversion of the ester-functional oxetane compound in a BOE-functional compound already takes place in the presence of a catalytic amount of a strong Brønsted or Lewis acid or organic complexes thereof. Lewis acids are preferred. Examples of Lewis acids are: $AlCl_3$, $SbCl_5$, $BF_3$, $BCl_3$, $BeCl_2$, $FeCl_3$, $FeBr_3$, $SnCl_4$, $TiCl_4$, $ZnCl_2$, and $ZrCl_4$ and organic complexes thereof, e.g., $BF_3Et_2O$, $BF_3$-$2CH_3COOH$, $BF_3$-$2H_2O$, $BF_3$—$H_3PO_4$, $BF_3$-$(CH_3)_2O$, $BF_3$-THF, $BF_3$-$2CH_3OH$, $BF_3$-$2C_2H_5OH$, and $BF_3$—$C_6H_5CH_2$. More preferred are $BF_3Et_2O$, $BF_3$-$2CH_3COOH$, and $SnCl_4$. Amounts of 0.001–0.1 mole of catalyst per mole of oxetane compound are preferred, more preferably 0.004–0.08 mole/mole. It has further been found that the conversion already takes place in the presence of a small amount of solvent, and even without solvent if so desired. The term solvent in this connection refers to those solvents which are conventionally employed in the field of organic chemistry and have been described for the conversion of oxetane compounds. The conversion takes place in the range of −100 to 200° C., preferably in the range of 0 to 80° C. The conversion time is in the range of 30 minutes to 2 days and can result in a yield of more than 90%.

Various methods can be employed to prepare SOE-functional compounds. One such method of preparation is the reaction of an epoxy-functional compound such as butyl glycidyl ether with a lactone such as caprolactone or butyrolactone. Alternatively, SOE-functional polymers can be prepared from epoxy-functional polymers, e.g., polyacrylates of glycidyl(meth)acrylate, using lactones, or from polylactones using monoepoxides. Again, use may be made of catalysts such as Lewis or Brønsted acids, preferably paratoluene sulphonic acid or $BF_3Et_2O$.

Further, a SOE-functional compound can be prepared by reacting pentaerythritol and triethyl orthopropionate in the presence of paratoluene sulphonic acid with a specific trimethyl benzene being used as solvent. Surprisingly, in this way very selectively a compound having two SOE groups of the following structure (V)

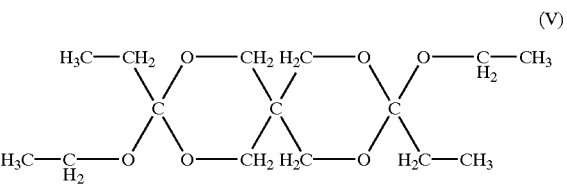

was synthesized.

The invention will be elucidated further with reference to the following examples.

EXAMPLES

In the examples the following abbreviations are used:

| | |
|---|---|
| paratoluene sulphonic acid | PTSA |
| dibutyl tin dilaurate | DBTL |
| methyl amyl ketone | MAK |
| ethyl amyl ketone | EAK |
| boron trifluoride etherate | $BF_3Et_2O$ |
| dibutyl phosphate | DBP |
| dodecyl benzene sulphonic acid | DDBSA |

In the examples the following compounds are used.
"EDENOR®" ME C6-10, ex. Henkel, a mixture of methyl ester of fatty acids, with the following chain length distribution: C6 1–8%, C8: 40–60%, C10: 30–50%, C12: 0–5%.
"BYK®" 333 is a silicone surface additive (available from Byk Chemie GMBH, Wesel, Federal Republic of Germany).

"BYK®" 300 is a flow additive, ex. Byk Chemie.
"BYK®" 322 is a flow additive, ex. Byk Chemie.
"BYK®" 355 is a flow additive, ex. Byk Chemie.
"DISPERBYK®" 110 is a dispersing agent, ex. Byk Chemie.
"DISPERBYK®" 166 is a dispersing agent, ex. Byk Chemie.
"NACURE®" 5076 is 70% DDBSA in isopropanol (available from King Industries, Inc., Norwalk, Conn.).
"FASCAT®" 4202 is a 10% DBTL solution in xylene (available from Elf Atochem North America, Philadelphia, Pa.).
"DESMODUR®" N3400 is an aliphatic polyisocyanate based on the uretdione of hexamethylene diisocyanate, ex. Bayer.
"DESMODUR®" VL50 is an aromatic polyisocyanate based on diphenylmethane diisocyanate, ex. Bayer.
"DESMODUR®" N3390 is an aliphatic polyisocyanate based on the isocyanurate of hexamethylene diisocyanate, ex. Bayer.
"DESMODUR®" L75 is an aromatic polyisocyanate based on toluene diisocyanate, ex. Bayer.
"DESMODUR®" LS2025 is an aliphatic low viscous polyisocyanate based on hexamethylene diisocyanate, ex. Bayer.
"VESTANAT®" T1890E is a cycloaliphatic polyisocyanate based on the isocyanurate of isophorone diisocyanate, ex. Hüls.
Hardener MS, ex. Sikkens, comprises "DESMODUR®" N3390 (S.C.=36%).

The polyester polyol A is a high solids polyester having a hydroxyl number of 148, an acid number of 8.8, and an Mn of 1888 (GPC, polystyrene standard). The polyester had a viscosity of 7 Pa.s in an 81%-solution in butyl acetate.

The polyester polyol B is based upon 1,4-dimethanol cyclohexane, hexahydrophthalic anhydride, 3,5,5-trimethyl hexanoic acid, trimethylol propane and glycidyl ester of a 1,1-disubstituted branched decane monocarboxylic acid. The polyester polyol has a solids content of 70%, a viscosity of 580 mPa.s at 20° C., a Tg of −3° C., an acid value of 0.2, a hydroxyl number of 160, a Mn of 1090 and a Mw of 3140 (as measured by gel permeation chromatography using polystyrene as a standard).

The polyester polyol C is based upon phthalic anhydride, hexahydrophthalic anhydride, 3,5,5-trimethyl hexanoic acid, and trimethylol propane. The polyester polyol has a solids content of 80.5%, a viscosity of 7.5 Pa.s at 20° C., a Tg of −2° C., an acid value of 9.3, a hydroxyl number of 145, a Mn of 1900 and a Mw of 4500 (as measured by gel permeation chromatography using polystyrene as a standard).

"AUTOCLEAR®" MS 2000, ex. Sikkens, comprises a polyacrylate polyol resin and 0.02% DBTL (on solids). The S.C. is 46%.

"RESIMENE®" RF 4518 is a melamine resin (available from Monsanto Company, St. Louis, Mo.).

"IRGAZIN®" DPP Red BO is a bright red pigment, ex. Ciba-Geigy. Zinc phosphate ZP10 is an anti-corrosive pigment, ex. Heubach.

"TIOXIDE®" TR92 is an titanium dioxide pigment (available from TioxideUK Limited, Durham, England).

"AEROSIL®" R972 is a silica compound (available from Degussa Aktiengesellschaft, Frankfurt, Federal Republic of Germany).

China clay grade C is an extender, ex. ECC International Ltd. Blank fix N is an extender, ex. Sachtleben Chemie GmbH.

"TINUVIN®" 1130 is a UV stabilizer, ex. Ciba-Geigy.
"TINUVIN®" 123 is a HALS stabilizer, ex. Ciba-Geigy.
"SOLVESSO" 100 is a blend of aromatic solvents, ex. Exxon. 1.2.3. Thinner slow, ex. Sikkens, is a mixture of solvents.

Unless otherwise stated, the properties of the coating compositions and the resulting films are measured as follows.

The viscosity was measured in a DIN flow cup number 4 according to DIN 53211–1987. The viscosity is reported in seconds.

The potlife is defined as the time period wherein the viscosity of the coating composition after initial mixing of all compounds is doubled.

The drying time is measured as follows. The coating composition is applied with a draw bar or by spraying onto steel plate. Using a BK Drying Recorder™ the time until the end of the third phase of the layer's drying is measured. The term third phase refers to the drying phase during which the BK Drying Recorder™'s needle makes a small, tight scratch in the film which no longer fills up.

A coating is "touch dry" when the mark formed by firm pushing with the thumb disappears after 1 or 2 minutes.

The solids content (S.C.) is measured after 1 day drying at room temperature followed by 1 hour at 150° C. The theoretical maximum S.C. is the S.C. at which all BOE or SOE is assumed to be hydrolyzed and bound in the dry film. The theoretical minimum S.C. is the S.C. at which it is assumed that all BOE or SOE has evaporated from the dry film.

Gloss is measured according to ISO 2813:1994. The gloss is expressed in Gloss units.

Solvent resistance is measured by exposing coated steel panels to MEK. The time required to soften the paint film to a pencil hardness of 2b gives the resistance.

EXAMPLE 1

Preparation of 4-methylol-1-methyl-2,6,7-trioxabicyclo[2.2.2]octane (BOE 1)

Into a flask equipped with a stirrer, a distilling column, a nitrogen inlet, a heating jacket, and a thermometer were charged 486 g of triethyl orthoacetate, 408 g of pentaerythritol, 300 g of diethylene glycol dimethyl ether, and 0.9 g of PTSA. The mixture was gradually heated to 170° C. over a period of 5 hours. During this time 490 g of distillate were obtained. The distillate contained mostly ethanol and small amounts of diethylene glycol dimethyl ether. The temperature was lowered to 100° C., and the remaining diethylene glycol dimethyl ether was distilled off under reduced pressure (30 mbar). The residue was subjected to vacuum distillation. The fraction having a boiling temperature of 126–130° C. at a pressure of 4 mbar yielded 426 g of oil. This oil solidified to a clear solid having a melting point of 99° C. and had the following structure

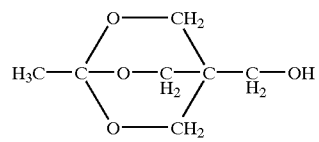

EXAMPLE 2

Preparation of 1,4-diethyl-2,6,7-trioxabicyclo[2.2.2]octane (BOE 2)

Into a flask as specified in Example 1 were charged 529 g of triethyl orthopropionate, 402 g of trimethylol propane, 330 g of diethylene glycol dimethyl ether, and 0.9 g of PTSA. The mixture was heated for 0.5 hour at 140° C., with 402 g of ethanol being distilled off. The temperature was lowered to 100° C., and the remaining diethylene glycol dimethyl ether was distilled off under reduced pressure. The residue was subjected to vacuum distillation. The fraction having a boiling temperature of 54° C. at a pressure of 0.5 mbar yielded 370 g of clear, low-viscous liquid having a boiling point of 223° C. at atmospheric pressure and with the following structure

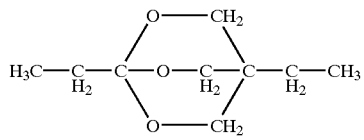

EXAMPLE 3

Preparation of a spiro-orthoester (SOE 1)

Into a flask as specified in Example 1 were charged 125 g of trimethyl benzene, 89 g of triethyl orthopropionate, 68 g of pentaerythritol, and 0.125 g of PTSA. The mixture was heated for 4 hours at 140° C. After just 2 hours the ethanol distillation came to a halt. In all, only 36 g of ethanol were distilled off. Only a portion of the pentaerythritol dissolved in the reaction mixture. After cooling the mixture was neutralized with potassium carbonate, and all solids were filtered off. Trimethyl benzene and traces of unreacted triethyl orthopropionate were distilled off under reduced pressure, and the residue was subjected to vacuum distillation. The fraction having a boiling temperature of 140–145° C. at a pressure of 1 mbar yielded 37 g of oil. After analysis via $^1H$ and $^{13}C$-NMR spectroscopy it was found that a spiro-orthoester compound of the following structure had formed

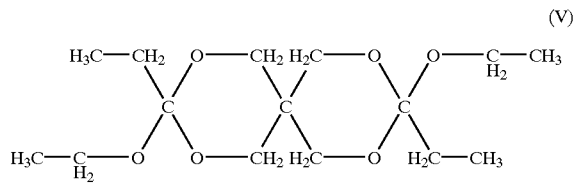

EXAMPLE 4

Preparation of a spiro-orthoester (SOE 2)

Into a flask equipped with a stirrer, a reflux condenser, a dropping funnel, a heating jacket, and a thermometer were charged 43 g of γ-butyrolactone, 65 g of diethyl ether, and 1.4 g of a 35%-solution of $BF_3Et_2O$ in diethyl ether. To this mixture were added in the course of 1 hour 93 g of butyl glycidyl ether. The reaction was slightly exothermic. By means of external cooling the temperature was maintained in the range of 23–28° C. After the addition of the butyl glycidyl ether the mixture was kept at said temperature for 3 hours with continuous stirring. Next, the reaction mixture was heated to reflux for one hour. After cooling to room temperature, 2 g of sodium carbonate were added and stirring was continued overnight at room temperature. The solids were filtered off, and 1 more g of sodium carbonate was added. Diethylether was distilled off at reduced pressure at room temperature. The residue was subjected to vacuum distillation. The fraction having a boiling point in the range of 45–65° C. at a pressure of 0.1 mbar yielded 31 g of clear liquid. After analysis ($^1H$ and $^{13}C$-NMR spectroscopy) it was found that a spiro-orthoester of the following structure had formed

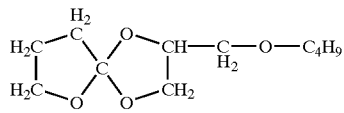

EXAMPLE 5

A: Preparation of 3-ethyl-3-hydroxymethyl oxetane

This oxetane was prepared as described by J. B. Pattison, J. Am. Chem. Soc., 79 (1957), p. 3455 and J. V. Crivello et al., J. M. S.-Pure Appl. Chem., A30 (1993), p. 189.

Trimethylol propane (1023.6 g, 7.63 moles), diethyl carbonate (901.3 g, 7.63 moles), and potassium hydroxide (0.77 g) were weighed into a 5-l three-neck flask. The reaction mixture was heated to reflux temperature (123° C). After the reaction temperature had been lowered to 105° C., the distilling off of ethanol was started. The reaction temperature was increased to 150° C. On conclusion of the distillation vacuum (15 mbar) was used to remove the remaining ethanol and diethyl carbonate from the reaction mixture. Next, the reaction mixture was heated to 220° C. Gas formation was observed, and under reduced pressure (40 mbar) at 130° C. a clear oil came over which was identified as 3-ethyl-3-hydroxymethyl oxetane. The yield was 698.0 g (79%); $^1H$ NMR (CDCl$_3$) d (ppm): 0.9 (t, $^3H$); 1.7 (q, $^2H$); 3.1 (t, $^1H$); 3.7 (d, $^2H$); 4.4 (dd, $^4H$).

B: Preparation of 3-ethyloxetan-3-yl methyl laurate

Into a three-neck flask (1 l) equipped with a Vigreux distillation column were weighed ethyl laurate (228.4 g, 1.0 moles), 3-ethyl-3-hydroxymethyl oxetane (116.0 g, 1.0 mole), dibutyl tin oxide (0.34 g), and xylene (25.0 g). The reaction mixture was heated to reflux temperature. At 170° C. ethanol began to distill off. The reaction mixture was heated such that the ethanol distillation proceeded smoothly. At a reaction temperature of 250° C. all ethanol had distilled off. The xylene was removed under reduced pressure. According to $^1H$ NMR analysis, the residue (298.7 g) was pure 3-ethyloxetan-3-yl methyl laurate. The product solidified at room temperature.

$^1H$ NMR (CDCl$_3$) d (ppm): 0.9 (2 x t, $^6H$); 1.3 (br s, $^{16}H$), 1.65 (m, $^2H$); 1.8 (q, $^2H$); 2.4 (t, $^2H$); 4.2 (s, $^2H$); 4.45 (dd, $^4H$).

C: Preparation of 4-ethyl-1-undecyl-2,6,7-trioxabicyclo[2.2.2]octane

This reaction was carried out under a nitrogen atmosphere. 3-ethyloxetan-3-yl methyl laurate prepared as specified in Example 5B (270.0 g, 904 mmoles) and BF$_3$Et$_2$O (1.0 g) were mixed in an Erlenmeyer flask. The reaction mixture was hazy but became clear after some time. After it had been left to stand overnight $^1H$ NMR analysis showed that virtually all oxetane ester had been converted into the corresponding BOE compound. The reaction mixture was subjected to a vacuum distillation. At 155° C./1 mbar 4-ethyl-1-undecyl-2,6,7-trioxabicyclo[2.2.2]octane came over. The yield was 205 g (76%). $^1H$ NMR (CDCl$_3$) d (ppm): 0.75 (t, $^3H$); 0.8 (t, $^3H$); 1.2 (br s, $^{16}H$); 1.35 (br m, $^2H$); 1.50 (t, $^2H$); 3.80 (s, $^6H$).

EXAMPLE 6

A: Preparation of 3-ethyl-3-hydroxymethyl oxetane

Trimethylol propane (1489 g, 11.1 moles), dimethyl carbonate (1201 g, 13.3 moles), and potassium hydroxide (5.38 g) were weighed into a 5-l three-neck flask equipped with a stirrer, a reflux condenser, a nitrogen inlet, a heating jacket, and a thermometer. The reaction mixture was heated to reflux temperature (86° C.) and kept at reflux for 2 hours. The temperature lowered to 80° C. Subsequently, the temperature of the reaction mixture was increased to 155° C. in 6 hours. On conclusion of the distillation 890 g distillate were obtained containing mostly methanol and dimethyl carbonate in a ratio of 60 to 40. The temperature was lowered to 120° C. and under vacuum (200–40 mbar) the remaining ethanol and dimethyl carbonate was removed from the reaction mixture (about 14 g). Next, the reaction mixture was gradual heated to 180° C. Under a stream of $CO_2$ and reduced pressure (60–40 mbar) a clear oil came over which was identified as 3-ethyl-3-hydroxymethyl oxetane. The yield was 860 g.

B: Preparation of 3-ethyloxetan-3-yl methyl ester of fatty acids

Into a flask (5 l) equipped as in Example 6A were weighed "EDENOR®" ME C6-10 (1268 g, 7.4 moles), 3-ethyl-3-hydroxymethyl oxetane of example 6A (858.4 g, 7.4 moles), and dibutyl tin oxide (2.13 g). The reaction mixture was heated to reflux temperature. At 150° C. methanol began to distill off. The reaction mixture was heated in 5 hours to 240° C. 197 g distillate were obtained comprising mainly methanol (83% of theory). The temperature was reduced to 150° C. and under vacuum (40 mbar) about 40 g of remaining distillate was removed. It was found that the residue (1834 g) had the following structure, wherein R is a mixture of pentyl, heptyl, nonyl, and undecyl groups:

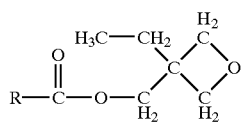

C: Preparation of crude 4-ethyl-1-(C5-11 alkyl)-2,6,7-trioxabicyclo[2.2.2]octane (BOE 3A)

This reaction was carried out under a nitrogen atmosphere. 3-ethyloxetan-3-yl methyl ester of fatty acids prepared as specified in Example 6B (1834 g) was cooled to 50° C. and $BF_3$-$2CH_3COOH$ (4.59 g) was carefully added thereto. The reaction mixture was heated to 70° C. and kept at that temperature for 6 hours. Next, the reaction mixture was cooled to 50° C. and 2.45 g triethyl amine was added to neutralize the catalyst. To the resulting residue 1% of a filter additive was added and filtrated. The filtrate was 1730 g and contained about 78% BOE and 22% polymer.

D: Preparation of pure 4-ethyl-1-(C5-11 alkyl)-2,6,7-trioxabicyclo[2.2.2]octane (BOE 3B)

Into a flask (5 l) equipped as in Example 6A were weighed 1730 g of crude BOE 3A prepared in Example 6C. The reaction mixture was heated to 140° C. and a reduced pressure of 40 mbar. The temperature was increased gradually to 240° C. whereby a clear liquid came over. 1235 g was collected of what was found to be pure BOE 3B of the following formula, wherein R is a mixture of C5, C7, C9, and C11 alkyl groups:

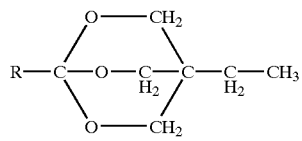

EXAMPLE 7

A: Preparation of dimethyl ester of dimer fatty acid

"PRIPOL®" 1009 dimer fatty acid, ex. Unichema (742 g, 1.31 moles, 2.62 eq. acid), methanol (2000 g), and "AMBERLYST®" t 15 acidic ion exchange resin from Rohm & Haas (Philadelphia, Pa.) (40 g) were weighed into a flask equipped with a stirrer, a reflux condenser, a nitrogen inlet, a thermocouple, and a heating jacket. The reaction mixture was heated to reflux temperature (65° C.). At intervals samples were analyzed by infrared spectroscopy. Heating was continued until the carbonyl signal of the carboxylic acid at 1710 $cm^{-1}$ disappeared in the infrared spectrum (about 18 hrs.). The reaction mixture was cooled to room temperature and the liquid decanted from the ion exchange resin. The liquid was subjected to rotary evaporation to evaporate substantially all methanol. The evaporation residue was diluted with diethylether (300 g). The ether solution was washed with, aqueous 10% sodium carbonate solution (500 g) and subsequently with water (500 g) in three portions. Magnesium sulfate (30 g) was added to the organic layer and stirred for 12 hrs. The liquid was filtered and the diethylether distilled off by rotary evaporation. The evaporation residue was the dimethyl ester of "PRIPOL®" 1009 as a colorless oil (752 g, 96% of theory).

B: Preparation of di-3-ethyloxetan-3-yl methyl ester of dimer fatty acid

Into a flask equipped with a stirrer, a distillation head, a nitrogen inlet, a thermocouple, a vacuum line, and a heating jacket were weighed the dimethyl ester of "PRIPOL®" 1009 of Example 7A (713.5 g, 2.4 eq.), 3-ethyl-3-hydroxymethyl oxetane of Example 6A (278.4 g, 2.4 moles), and dibutyl tin oxide (1.0 g). The reaction mixture was gradually heated in 4 hours to 240° C. During this time 47 g methanol were distilled off. The temperature was reduced to 160° C. and vacuum was applied. The pressure was gradually decreased to 20 mbar during 3 hours. Residual methanol was distilled off during this time. When distillation had ceased, the reaction mixture was cooled to room temperature. The light yellow oily product is analyzed by infrared spectroscopy. There was no hydroxyl signal at 3400 $cm^{-1}$ visible in the infrared spectrum. The yield was 914 g.

C: Preparation of the BOE derivative of di-3-ethyloxetan-3-yl methyl ester of dimer fatty acid (BOE 4)

In a flask equipped as in Example 7A were weighed di-3-ethyloxetan-3-yl methyl ester of dimer fatty acid prepared as specified in Example 7B (914 g) and butyl acetate (1400 g). At room temperature $BF_3$-$Et_2O$ (9.15 g) was added thereto during 15 minutes. The reaction mixture was heated to 50° C. and kept at that temperature for 10 hours. Next, the reaction mixture was cooled to room temperature and 6.5 g triethyl amine was added. A precipitate was formed, which was filtered off. The product analyzed by infrared spectroscopy showed a small signal at 3400 $cm^{-1}$ indicating hydroxyl functionality. Phenyl isocyanate (9 g) was added to the product. After 1 hour at room temperature infrared spectroscopy indicated the absence of hydroxyl functionality (no signal at 3400 cm$^{-1}$) and of isocyanate functionality (no signal at 2270 cm$^{-1}$). Part of the butyl acetate was evaporated. The final product has a solids content of 82.7% and is a yellow oil.

EXAMPLE 8

A: Preparation of an oxetane-functional polyester

Diethyl malonate (686.0 g, 4.3 moles), neopentylene glycol (358.1 g, 3.45 moles), 3-ethyl-3-hydroxymethyl oxetane (196.2 g, 1.7 moles), dibutyl tin oxide (1.2 g), and xylene (100 g) were weighed into a 2 l three-neck flask equipped with a distilling set-up. The reaction mixture was heated to reflux temperature. At 189° C. the ethanol distillation began. The distillation speed was controlled by slowly increasing the reaction temperature. At a temperature of 210° C. all ethanol had been distilled off. The xylene was removed from the reaction mixture under reduced pressure. The obtained oxetane-functional polyester had a molecular weight of Mn=1021 and Mw=1875 (GPC, polystyrene standard).

B: Preparation of a BOE-functional polyester

This reaction was carried out under a nitrogen atmosphere. Into a round-bottomed flask were weighed: the oxetane-functional polyester as prepared in Example 8A (800.0 g, 1.6 equivalents of oxetane) and BF$_3$Et$_2$O (about 1 g). An exothermic reaction took place. The temperature of the reaction mixture rose to 62° C. Next, there was cooling with a water bath. After one night virtually all oxetane groups were found to have been converted into the corresponding BOE groups (BOE signal at d (ppm) 4.0 in $^1$H NMR). The obtained BOE-functional polyester had a molecular weight of Mn=1648 and Mw=7449 (GPC, polystyrene standard).

EXAMPLE 9

A: Preparation of 3-ethyloxetan-3-yl methyl acrylate

The synthesis was carried out as described by P. G. Gassman et al., *Chem. Comm.*, (1989), p. 837.

The reaction was carried out under a nitrogen atmosphere. To a mixture of 3-ethyl-3-hydroxymethyl oxetane (170.6 g, 1.50 moles) and triethyl amine (153.8 g, 1.52 moles) in tetrahydrofuran (500 g) cooled in an ice bath acryloyl chloride (137.5 g, 1.52 moles) was added dropwise. The reaction mixture was stirred for one hour at room temperature. To the reaction mixture 500 g of water were added. The organic layer was separated from the aqueous layer. The aqueous layer was extracted with diethyl ether (2×500 ml). The combined organic layers were dried with a saturated NaCl solution and magnesium sulphate. Following filtration of the ether layer the volatile organic compounds were removed under vacuum using a rotary vacuum evaporator. The residue was distilled under vacuum. 3-ethyloxetan-3-yl methyl acrylate was isolated at 122° C./19 mbar as a clear oil. The yield was: 200.4 g, (80%). $^1$H NMR (CDCl$_3$) d (ppm): 0.92 (t, $^3$H); 1.80 (q, $^2$H); 4.30 (s, $^2$H); 4.48 (dd, $^4$H); 5.88 (d, $^1$H); 6.18 (dd, $^1$H); 6.45 (d, $^2$H).

B: Preparation of a polyacrylate having BOE-functional side groups

A mixture of butyl acrylate (38.0 g), trimethyl cyclohexyl methacrylate ("NOURYCRYL MC™" 109, 45.0 g), 3-ethyloxetan-3-yl methyl acrylate (17.0 g), t-butylperoxy-3,5,5-trimethyl hexanoate ("TRIGONOX®" from Akzo Chemie Nederland BV, Amersfoort, Netherlands 42S, 3.0 g), and dodecyl mercaptan (2.0 g) was added over a period of 2 hours to refluxing MAK (42.7 g). During the feeding the temperature rose from 155° C. to 169° C. After the feeding there were two further additions, each over 30 minutes, of a solution of "TRIGONOX®" 42S (0.25 g) in MAK (1.0 g). The reaction mixture was cooled to room temperature. Next, BF$_3$Et$_2$O (0.75 g) was added. The obtained resin had the following physical properties: Mn=1736, Mw=4567, viscosity 1.28 Pa.s, and S.C.=74.7% (after 30 minutes of heating at 150° C.).

EXAMPLE 10 AND COMPARATIVE EXAMPLE A

BOE as main binder reacting with a polyisocyanate-containing compound

"DESMODUR®" N3390 was mixed with (2,2-dimethylol-n-butyl)propionate (DBP) and BOE 2, respectively (130 eq. % NCO, calculated on (latent) hydroxyl). 0.15 wt. % of DBTL, calculated on solid matter, and 0.33 wt. % of PTSA, calculated on DBP, were added to the DBP mixture, while 0.15 wt. % of DBTL calculated on solid matter and 0.83 wt. % of PTSA calculated on BOE 2 were added to the BOE 2 mixture. The two mixtures were diluted with a 50:50 mixture of MAK/EAK to spraying viscosity (±DINC4 18"). 270 g of MAK/EAK were needed to give the DBP mixture the desired spraying viscosity. By contrast, the BOE 2 mixture required only 200 g. The use of BOE 2, in other words, makes for a 70 g reduction of the amount of diluent required to obtain a sprayable composition. The pot life and drying time data is compiled below. Pot life is defined as the time during which the viscosity of the coating composition increased to 30" DINC4. The coating compositions were sprayed on a steel plate to obtain a 50μ layer after drying. It is obvious that the coating composition according to the present invention has a longer pot life and a shorter drying time, in other words, an especially favorable pot life:drying time ratio.

| Example | | Pot life | Drying time (min.) |
|---|---|---|---|
| A | DBP | 10 min. | 140 |
| 9 | BOE 2 | >1 day | 100 |

EXAMPLE 11 AND COMPARATIVE EXAMPLE B

SOE as main binder reacting with a polyisocyanate-containing compound

Two samples of SOE 2 were mixed with "DESMODUR®" N3390 (130 eq. % of NCO, calculated on latent hydroxyl), 0.3 wt. % of DBTL, calculated on solid matter, was added to the two mixtures, while 1.1 wt. % of PTSA, calculated on SOE 2, was added to one of the mixtures. The coating compositions were applied on a steel plate with a 100μ draw bar. The S.C. results are compiled below. They clearly show the effect PTSA has on the deblocking of the hydroxyl groups in the SOE composition.

|         |         | S.C.            |          |
|---------|---------|-----------------|----------|
| Example | PTSA    | max. theoretical | measured |
| 11      | 1.1 wt. % | 83.6%         | 80.4%    |
| B       | —       | 83.6%           | 59.1%    |

EXAMPLES 12–18

BOE as main binder reacting with a polyisocyanate-containing compound 4.3 parts by weight of BOE 2 were mixed with 10.8 parts by weight of "DESMODUR®" N3390 (100 eq. % NCO, calculated on latent hydroxyl). 0.3 wt. % of DBTL, calculated on solid matter, was added. Various acids were added as catalysts for the hydrolysis of the B.E compound. The coating compositions were applied on steel plates with a 100μ draw bar. The data is compiled below. The percentages of catalyst mentioned in the table are based on the amount of BOE 2. PTSA has a pKa of 0.5–1, the pKa of benzoic acid (BZ) is 4.2, and the pKa of DBF is 2–3. The S.C. is measured after 1 day drying at room temperature and 1 hour at 120° C.

| Example | Cat.(%) | S.C. film | Max. S.C. theor. | Min. S.C. theor. | Gelling time | Touch dry time |
|---------|---------|-----------|------------------|------------------|--------------|----------------|
| 12      | —       | 72.2      | 93.2             | 62.6             | >1 week      | 3 hrs.         |
| 13      | 1.63 ZnCl₂ | 64.3   | 92.4             | 60.6             | >1 week      | 1 hr.          |
| 14      | 1.63 BZ | 70.2      | 89.2             | 56.6             | >1 week      | 2 hrs.         |
| 15      | 0.47 PTSA | 71.4    | 92.4             | 62.0             | >1 week      | 4 hrs.         |
| 16      | 1.63 PTSA | 89.4    | 92.4             | 60.6             | >1 week      | 3 hrs.         |
| 17      | 1.63 BF₃Et₂O | 87.5 | 92.4             | 60.6             | >1 week      | >4 hrs.        |
| 18      | 1.63 DBP | 88.0     | 92.4             | 60.6             | >1 week      | >5 hrs.        |

In all cases there is excellent pot life. The S.C. improves with the use of stronger acid or larger quantities of acid. Example 16 provides the best results with a high S.C. and a reasonable drying time.

COMPARATIVE EXAMPLES C AND D

Example 12 was repeated. Instead of 4.3 parts of BOE 2, 3.7 parts of 2-ethyl-1,3-hexane diol were added. Two mixtures were prepared comprising 0.005 parts by weight and 0.05 parts by weight of DBTL, calculated on solid matter, respectively. For the first mixture a pot life of 0.5 hour was measured, for the second, one of 1 minute. The touch dry time of the coating composition when using 0.05 parts by weight of DBTL was over 4 hours at room temperature.

EXAMPLE 19 AND COMPARATIVE EXAMPLE E

BOE as reactive diluent in a composition comprising a polyester polyol and a polyisocyanate-functional compound The diluting capacity of BOE 2 was compared with ethylbutyl propane diol (EBP), a hydroxyl-functional compound, in a high solids urethane coating formulation. Use was made of 130 eq. % NCO ("DESMODUR®" N3390) on (latent) hydroxyl. Polyester polyol A was used as the binder. The catalyst used for the BOE hydrolysis was PTSA, the catalyst for the isocyanate-hydroxyl reaction was DBTL. It can be seen from the table that when BOE 2 is used, there is 65 grams less solvent present per kilogram of paint (about 65 grams per liter). Because of the lower equivalent weight of BOE 2 in comparison with EBP, comparatively speaking a little more isocyanate is needed for cross-linking. All amounts are in parts by weight.

|                  | Example E | Example 19 |
|------------------|-----------|------------|
| Polyester A      | 40        | 40         |
| BOE 2            | —         | 8.1        |
| EBP              | 8.1       | —          |
| Desmodur ® N3390 | 54.4      | 61.9       |
| DBTL             | 0.12      | 0.06       |
| PTSA             | —         | 0.4 (4.9 wt. % calc. on BOE 2) |
| MAK              | 30.8      | 26.3       |
| EAK              | 16        | 9.5        |
| Shellsol D       | 7.34      | 8.4        |
| Viscosity (DINC4)| 18.2"     | 17.6"      |

EXAMPLE 20 AND COMPARATIVE EXAMPLE F

BOE as main binder with a polyisocyanate-functional compound

The performance of BOE 2 was compared with that of a commercially available reactive diluent, Oxazolidine "ZOLDINE®" RD20 (available from Angus Chemical Company, Buffalo Grove, Ill.) (1-aza-3,7-dioxo-bicyclo-2,8-diisopropyl-5-ethyl-[3,3,0]-octane).

"DESMODUR®" N3390 was cross-linked with the two compounds (130 Eq. % NCO, calculated on (latent) hydroxyl). The coating compositions were diluted with MAK:EAK (50:50) to a viscosity of 19" DINC4. Added were 0.1 wt. % of DBTL, calculated on solid matter, and 0.57 wt. % of PTSA, calculated on BOE 2. Both compositions were sprayed onto bare steel. The temperature during drying was 20° C., the relative humidity 70%. Below it can be seen that the pot life is longer when use is made of BOE 2, while drying proceeds more rapidly.

| Example |           | Viscosity after 6 hrs. (DINC4) | Drying (min.) |
|---------|-----------|--------------------------------|---------------|
| 20      | BOE 2     | 23"                            | 175           |
| F       | Zoldine ® | 29"                            | 400           |

EXAMPLES 21 AND 22 AND COMPARATIVE EXAMPLE G

BOE as main binder in combination with a polyisocyanate-functional compound and an acid generating initiator.

A coating composition was prepared containing
5.3 parts by weight of BOE 3B
10.8 parts by weight of "DESMODUR®" N3390
1.5 parts by weight of 10% DBTL in butylacetate 1.06 parts by weight of 20% 2-methyl-1-[4-(methylthio) phenyl]-2-[4-methylphenylsulphonyl] propan-1-one (MDTA), ex. Fratelli Lamberti Spa, Varese, Italy, in butyl acetate.

The coating composition was applied with a draw bar onto two steel plates to give a 50 μm film thickness after drying. Five minutes after application one steel plate was irradiated by UV-A for 1 minute (Example 21). After an hour at room temperature the coating was touch dry and clear. The unradiated coating (comparative example G) was touch dry after 5 hours but was very troubled due to unhydrolyzed BOE. The coating composition was stored for a week at 50° C. Then it was applied as described above (example 22). The coating was again touch dry after an hour. The storage stability of the MDTA containing coating composition is very good.

EXAMPLE 23 AND COMPARATIVE EXAMPLE H

BOE as main binder with a Polyacetal-functional resin

Two coating compositions were prepared as listed below (all amounts in parts by weight). The polyacetal-functional resin is a copolymer of glycerol cyclocarbonate methacrylate and styrene, upon which amino butyraldehyde dimethyl acetal is adducted (S.C.=62% in butyl acetate (wt. eq. acetate groups=951)). BOE 4 has a S.C. of 83% in butylacetate, the wt. eq. BOE=476). "NACURE®" was diluted to a 10% solution in butyl acetate.

As can be seen from the results listed below the composition of the present invention has an excellent potlife. The coating compositions were applied with a draw bar onto a steel plate to give a 50 μm film thickness after drying. The touch dry time of the coating composition of the present invention is equal to the comparative coating composition as well as the solvent resistance to MEK.

|  | Example 23 | Comparative Example H |
|---|---|---|
| polyacetal-functional resin | 9.5 | 9.5 |
| BOE 4 | 4.8 | — |
| Hydrolyzed BOE 4 | — | 4.8 |
| 10% Nacure 5076 | 1.0 | 1.0 |
| gel time in the pot | >2 weeks | 5 hours |
| Touch dry time | 10 minutes | 10 minutes |
| MEK resistance after 1 week | 2 | 2 |

EXAMPLE 24 AND COMPARATIVE EXAMPLE I

BOE as main binder with polyalkoxysilane-functional resin

Two coating compositions were prepared as listed below (all amounts in parts by weight). The polyalkoxysilane-functional resin is an adduct of 1 mole of diethyl malonate and 2 moles of 3-amino propyl trimethoxy silane, i.e. AMEO-T ex. Wacker (S.C.=95.6% in xylene (wt. eq. Si(EtO)$_3$ groups=255)). BOE 4 has a S.C. of 83% in butylacetate, the wt. eq. BOE=476). "NACURE®" 5076 was diluted to a 10% solution in butyl acetate.

As can be seen from the results listed below the composition of the present invention has an excellent potlife. The coating compositions were applied with a draw bar onto a steel plate to give a 50 μm film thickness after drying. The touch dry time of the coating composition of the present invention is equal to the comparative coating composition as well as the solvent resistance to MEK.

|  | Example 24 | Comparative Example I |
|---|---|---|
| polyalkoxysiloxane-functional resin | 5.1 | 5.1 |
| BOE 4 | 4.8 | — |
| Hydrolyzed BOE 4 | — | 4.8 |
| 10% Nacure 5076 | 0.9 | 0.9 |
| gel time in the pot | >2 weeks | 1 hours |
| Touch dry time | 20 minutes | 20 minutes |
| MEK resistance after 1 week | 2 | 2 |

EXAMPLE 25

BOE as main binder with a melamine resin

A coating compositions was prepared as listed below (all amounts in parts by weight).

|  | Example 25 |
|---|---|
| Resimene RF 4518 | 8 |
| BOE 3B | 2 |
| Nacure 5076 | 0.6 |
| gel time in the pot | <1 hour |
| Touch dry time | 1.5 hours |
| MEK resistance after 1 week | 2 |

The results listed above show that a composition comprising a melamine resin and a catalyst frees water which result in a very quick ring opening of the BOE compound. Accordingly, the potlife is very short and this coating composition asks for a 2K component system or a blocked catalyst. The coating composition was applied with a draw bar onto a steel plate to give a 50 μm film thickness after drying.

EXAMPLES 26 AND 27

Solvent free clearcoat compositions

Two solvent free clearcoat compositions were prepared as listed below. The coatings were made according to a 3 pack system. The first component contained the BOE compound, the second component contained the polyisocyanate compound and the third component contained the acid catalyst. Solvent-free is defined as VOC<100 g/l.

| Component | Compound | Example 26 | Example 27 |
|---|---|---|---|
| 1 | BOE 3B | 34.2 g | 30.2 g |
|  | Caster oil | — | 6.0 g |
|  | DBTL | 0.51 g | 0.54 g |
|  | Byk 333 | 0.41 g | 0.44 g |
| 2 | Desmodur ® N3400 | 63.5 g | 46.5 g |
|  | Desmodur ® VL50 | — | 14.8 g |
| 3 | Nacure 5076 | 1.37 g | 1.45 g |

Both compositions have a viscosity of 23" (DINC4). The clearcoats were sprayed on steel panels coated with "AUTOBASE®" MM basecoat, ex. Sikkens, with a high volume low pressure spraygun (HVLP). The coatings were cured at room temperature and 60° C. Appearance was excellent, good gloss, and good flow/leveling. Stone chip resistance, solvent resistance and adhesion were good.

EXAMPLES 28 AND 29

Solid color topcoat compositions

Two solid color topcoat compositions were made based on BOE. In the first composition the pigment was dispersed in BOE, while in the second composition a pigment paste based on polyester is used. Component 1 was milled on a bead mill until the particle size was smaller than 10µ.

| Component | Compound | Example 28 | Example 29 |
|---|---|---|---|
| 1 | BOE 3B | 37.5 g | — |
|  | polyester polyol B | — | 45.0 g |
|  | Irgazin DPP Red BO | 33.6 g | 24.7 g |
|  | Disperbyk 166 | 16.8 g | 17.0 g |
|  | Butylacetate | 6.1 g | 6.6 g |
|  | Solvesso 100 | 6.1 g | 6.6 g |
| 2 | BOE 3B | 34.8 g | 28 g |
|  | Desmodur ® N3390 | 141.4 g | 80 g |
|  | DBTL | 1.08 g | 0.96 g |
| 3 | Nacure 5076 | 1.44 g | 0.56 g |
|  | Solvesso 100 | 17.0 g | 4.0 g |
|  | Ethoxyethyl propionate | 17.0 g | 4.0 g |

Both coating compositions were sprayed on steel panels prepared with a conventional primer as a car refinish topcoat. Appearance and application behavior is good. The VOC level is at a very low level, approximately 250 g/l.

EXAMPLES 30 AND 31

Clearcoat coating compositions

Two clearcoat coating compositions were prepared as listed below. Both coating compositions have a viscosity of 16" DINC4. Potlife of the coating composition of Example 30 is shorter than the potlife of the coating composition of Example 31, due to the presence of hydroxyl-functional polymer in BOE 3A. Both clearcoat compositions were sprayed on steel panels prepared with "AUTOBASE®" MM basecoat, ex. Sikkens, using a HVLP spraygun. Room temperature cure of the coating composition of Example 30 is faster than the cure of the coating composition of Example 31. Appearance and gloss of both coatings are excellent.

| Component | Compound | Example 30 | example 31 |
|---|---|---|---|
| 1 | BOE 3A | 40 g | — |
|  | BOE 3B | — | 40 g |
|  | DBTL (10% in butylacetate/xylene (1/1)) | 4 g | 4 g |
|  | Byk 322, Byk 355, butylacetate (20/15/65) | 2 g | 2 g |
|  | Solvesso 100/ethoxyethyl proprionate (1/1) | 14 g | 24 g |
| 2 | Desmodur ® N3390 | 67.6 g | 78.5 g |
| 3 | Nacure 5076 | 1.14 g | 1.14 g |

EXAMPLES 32 AND 33

Clearcoat coating compositions

Two clearcoat coating compositions were prepared as listed below. Both clearcoat compositions were sprayed on steel panels prepared with "AUTOBASE®" MM basecoat, ex. Sikkens, using a HVLP spraygun. Both clearcoats have excellent paint properties. Application properties are very good. Appearance and gloss are excellent.

| Component | Compound | Example 32 | Example 33 |
|---|---|---|---|
| 1 | BOE 3B | 34 g | 34 g |
|  | polyester polyol B | 7.5 g | — |
|  | polyester polyol C | — | 7.5 g |
|  | DBTL (10% in butylacetate/xylene (1/1)) | 40 g | 40 g |
|  | Byk 322, Byk 355, butylacetate (20/15/65) | 8.56 g | 8.56 g |
|  | Solvesso 100 | 5.6 g | 5.6 g |
|  | Ethoxyethyl proprionate | 5.6 g | 5.6 g |
|  | Tinuvin 1130 | 0.1 g | 0.1 g |
|  | Tinuvin 123 | 0.05 g | 0.05 g |
| 2 | Desmodur ® N3390 | 71.0 g | 71.0 g |
| 3 | Nacure 5076 | 0.98 g | 0.98 g |

EXAMPLES 34 AND 35

Primer compositions

Two ultra high solid primer compositions were prepared as listed below. Component 1 was stirred at high speed for 15 minutes and subsequently passed twice through a closed mill to obtain a fineness of less than 25 µm. Component 1 was then mixed with premixed components 2 and 3.

| Component | Compound | Example 34 | Example 35 |
|---|---|---|---|
| 1 | BOE 3B | 17.0 g | 17.0 g |
|  | Disperbyk 110 | 1.4 g | 1.4 g |
|  | Tioxide TR92 | 21.0 | 21.0 |
|  | Zinc phosphate ZP10 | 13.6 | 13.6 |
|  | Blank fix N | 11.0 | 11.0 |
|  | China clay grade C | 23.5 | 23.5 |
|  | Aerosil R972 | 0.8 | 0.8 |
|  | Solvesso 100 | 6.0 | 6.0 |
|  | Ethoxyethyl propionate | 5.9 | 5.9 |
| 2 | Fascat 4202 | 0.25 | 0.25 |
|  | Nacure 5076 | 0.35 | 0.35 |
|  | Byk 300 | 0.8 | 0.8 |
| 3 | Desmodur ® L75 | — | 23.4 |
|  | Vestanat ® T1890E | 25.1 | — |
|  | Desmodur ® LS 2025 | 25.1 | 25.1 |
|  | Butyl acetate | 4.0 | 4.3 |
|  | Solvesso 100 | 7.0 | 7.5 |

Both primer coating compositions were applied with conventional spray equipment on steel panels and had a spray viscosity around 2.0 Poise (measured with a Sheen Rotothinner) at a VOC around 290 g/l. Dried at room temperature (overnight) or at 60° C. (30 minutes), hard and good sandable coatings were obtained which can be topcoated with regular car refinish topcoat systems and/or coating compositions of the present invention such as exemplified in Examples 26–29 (pigmented topcoats as well as base/clear systems).

Advantages over existing Medium Solid 2k primer/filler materials as used in the car refinish market nowadays are: a very low VOC, a long potlife and a high build behavior. Compared to existing High Solids primer compositions comprising imine crosslinkers advantages are again a long potlife, fast drying at 60° C., and the fact that there is no emission of volatile blocking components (like aldehydes and ketones from crosslinkers such as ketimines, aldimines and oxazolidines).

EXAMPLES 36, 37, AND 38 AND COMPARATIVE EXAMPLE J

BOE 3B as reactive diluent in a clearcoat coating composition

A commercial available clearcoat component Sikkens "AUTOCLEAR®" MS 2000 was diluted with different amounts of BOE 3B. Compositions are listed below. Component 1 was mixed with components 2 and 3 and sprayed on steel panels prepared with "AUTOBASE®" MM basecoat, ex. Sikkens, using a HVLP spraygun.

| Component | Compound | C. Ex. J | Ex. 36 | Ex. 37 | Ex. 38 |
|---|---|---|---|---|---|
| 1 | MS 2000 | 100 | 100 | 100 | 100 |
|   | BOE 3B |  | 4.4 | 11.1 | 17.8 |
|   | DBTL |  | 0.2 | 0.9 | 1.6 |
|   | Acetyl acetone |  | 0.3 | 1.1 | 1.9 |
|   | Nacure 5076 |  | 0.1 | 0.3 | 0.5 |
| 2 | Hardener MS Standard | 50 |  |  |  |
|   | Desmodur ® N3390 |  | 32.6 | 43.1 | 53.6 |
| 3 | 1.2.3. Thinner slow | 9.4 | 33 | 35 | 35 |

| Properties | C. Ex. J | Ex. 36 | Ex. 37 | Ex. 38 |
|---|---|---|---|---|
| VOC (g/l) | 560 | 529 | 498 | 468 |
| Viscosity (DINC4, sec.) | 18 | 18 | 19 | 19 |
| ratio NCO/OH | 78 | 100 | 100 | 100 |
| Touch dry (60° C., min.) | 30 | 10 | 10 | 10 |
| Touch dry (RT, min.) | 120 | 120 | 77 | 60 |
| Potlife (min.) | >180 | 60 | 60 | 60 |
| Gloss | 74 | 86 | 82 | 83 |

The addition of BOE 3B as a reactive diluent results in a VOC reduction, a decrease in drying time, and an increase in gloss.

We claim:

1. A process for the preparation of a compound comprising at least one bicyclo-orthoester group comprising converting a compound having at least one corresponding oxetane group in the presence of a catalytic amount of a compound selected from the group consisting of a strong Brønsted acid, Lewis acid and organic complexes thereof, wherein the catalyst is employed in an amount of 0.001–0.1 mole of catalyst per mole of oxetane group.

2. The process of claim 1 wherein the Lewis acid is selected from the group consisting of $BF_3Et_2O$, $BF_3\text{-}2CH_3COOH$, and $SnCl_4$.

3. The process of claim 1 wherein the reaction takes place in the presence of a small amount of solvent.

* * * * *